United States Patent [19]

Tamanoi

[11] Patent Number: 5,578,477
[45] Date of Patent: Nov. 26, 1996

[54] IDENTIFICATION AND CHARACTERIZATION OF INHIBTORS OF PROTEIN FARNESYLTRANSFERASE

[75] Inventor: Fuyuhiko Tamanoi, Chicago, Ill.

[73] Assignee: Arch Development Corporation, Chicago, Ill.

[21] Appl. No.: 931

[22] Filed: Jan. 5, 1993

[51] Int. Cl.⁶ .............................. C12N 9/10; A61K 38/45
[52] U.S. Cl. ........................................ 435/793; 424/94.5
[58] Field of Search ............................ 435/193; 424/94.5

[56] References Cited

U.S. PATENT DOCUMENTS 5,141,851  8/1992  Brown et al. ............................ 435/15
5,420,245  5/1995  Brown et al. ............................ 530/328

OTHER PUBLICATIONS

Omer et al., Mol. Microbiol. 11:219–225 (1994).
Goodman, PH.D Thesis, Univ. Of Chicago, 1991, pp. 46–84.

Primary Examiner—Robert A. Wax
Assistant Examiner—Eric Grimes
Attorney, Agent, or Firm—Brinks Hofer Gilson & Lione

[57] ABSTRACT

A method of purifying protein farnesyltransferase (Ftase) uses recombinant technology and yeast host cells. Yeast farnesyltransferase purified by the method is useful in confirming specificity and kinetics of potential protein farnesyltransferase inhibitors. These inhibitors are useful for chemotherapy directed against cancers related to ras oncogenes.

5 Claims, 6 Drawing Sheets

IDENTIFICATION AND CHARACTERIZATION OF INHIBTORS OF PROTEIN FARNESYLTRANSFERASE

The United States Government may own certain rights in the present invention pursuant to a grant from the National Institutes of Health (CA 41996), the United States Public Health Service.

BACKGROUND OF THE INVENTION

Protein farnesyltransferase (FTase) is a key enzyme that is responsible for the post-translational modification of a number of proteins involved in cell growth. These proteins include ras proteins, nuclear lamins and the yeast a-mating factor, all of which end with a unique C-terminal sequence, (SEQ. ID. NO. 1) CAAX (where A is an aliphatic amino acid and X is the C-terminal amino acid) termed the 'CAAX box'. FTase catalyses the addition of a farnesyl group to the cysteine.

Ras proteins have been implicated in oncogenesis. Ras proteins are farnesyl acceptors. In the case of ras proteins, farnesylation contributes to an increase in their hydrophobicity, thus facilitating their membrane localization. Because a proper membrane localization is required for the function of ras proteins, inhibiting their membrane localization may block the action of oncogenic forms of the ras protein.

Several approaches to block ras function have been proposed. These include reversal of impaired GTPase activity of the oncogenic ras molecule and inhibition of ras interaction with its target or effector molecule. The most promising may be to interfere at the level of ras membrane localization by using specific drugs that inhibit ras FTase. Inhibitors of FTase so far reported include prenyl substrate analogues or synthetic peptides that correspond to the ras CAAX motif. However, intracellular delivery of these inhibitors may present a problem. For prenyl substrate analogues, the diphosphate prevents cell penetration. As for peptides, cellular uptake may also be inefficient and degradation in intestinal cells may be rapid. Non-peptide and non-prenyl diphosphate type inhibitors are suitable for development as potent orally active long-duration therapeutic agents.

Inhibition of ras farnesylation in vivo was demonstrated with compactin, but, this drug inhibits HMG-CoA reductase and acts as a general inhibitor of the isoprenoid pathway, and is unlikely to be useful for specifically antagonizing ras function. On the other hand, an inhibitor of ras farnesyltransferase, the key enzyme that catalyzes the farnesylation, would not perturb other elements of the mevalonate pathway, and therefore, would be expected to be a more effective antagonist of ras function. Searches for such inhibitors requires detection assays and methods of confirming the specificity and kinetics of the inhibitors.

FTase from rat brain has been characterized. This enzyme has strong affinity to the CAAX sequence. It binds to a column containing peptides having the CAAX sequence and is inhibited by tetrapeptides containing the CAAX sequence. The tetrapeptide inhibition was useful in the determination of sequence requirements for the CAAX box. The mammalian enzyme is a heterodimer consisting of two similar sized subunits termed α and β. The β subunit can be cross-linked to ras proteins, suggesting that the site of CAAX recognition is within the β-subunit. Purification of FTase from this source requires peptide affinity chromatography as a final step. This step is difficult to reproduce. Large-scale production of purified mammalian enzyme is not available, in particular, by recombinant technology.

An FTase similar to the mammalian enzyme was detected in crude extracts of yeast cells. Two genes, designated DPR1 or RAM1 (referred to herein as DPR1), and RAM2, respectively, are required for the yeast FTase activity. A possible explanation is that the enzyme consists of two subunits encoded by these genes. This hypothesis is strengthened by the detection of a significant (approximately 30%) identity between the expression product of DPR1 and the β-subunit of the mammalian FTase as well as between the expression product of RAM2 and the α-subunit of the mammalian FTase. Levels of expression, however, are too low for adequate processing, for example, purification. FTase activity of crude extracts was also detected by transfer activity of farnesyl onto a substrate after simultaneous expression of DPR1 and RAM2 genes in *Escherichia coli,* but the enzyme was neither overproduced nor purified.

In the present invention a surrogate for mammalian FTase was sought. Recombinant technology was used to overproduce FTase. Yeast was selected as a host cell to attempt to enhance production of FTase so that sufficient protein was available for purification. Multiple copies of genes for both subunits of protein FTase were introduced into the host cell to overproduce the enzyme. Unexpected synergism resulted, making it possible to achieve the purification goal. FTase was found to be an acceptable surrogate for mammalian FTase in tests for inhibitors. Either mammalian or yeast gene sequences may be used for expressing the enzyme. A purification involving one column is all that is subsequently required to purify the enzyme to near homogeneity. The purified enzyme is useful for confirming the specifity and kinetics of FTase inhibitors.

SUMMARY OF THE INVENTION

In the search for effective chemotherapeutic agents against ras-related cancers, the farnesylation step is a promising target. Farnesylation is an essential post-translational modification of ras proteins necessary for membrane archoring. Disruption of this step, therefore, interferes with the action of the ras oncogene in producing malignant growth. Farnesylation of the ras proteins is effected by farnesyltransferase, an enzyme which has been identified in rat brain and in yeast. A method of disrupting ras farnesylation would, therefore, be to disrupt the action of farnesyltransferase. This disruption results from exposure of the enzyme to an inhibitor of farnesyltransferase. Incorporating a suitable inhibitor in a pharmacologically acceptable composition would produce an effective chemotherapeutic agent.

Although some inhibitors of farnesyltransferase are known, for example, a tetrapeptide containing CAAX, there are limitations preventing progress of these into clinical use. These limitations include lack of specificity, leading to undesirable disruption of other biochemical pathways, inability of the drug to enter the cell (permeability) and insufficient inhibition. The search for appropriate, clinically effective inhibitors is ongoing. To facilitate the search, a method to identify and characterize farnesyltransferase inhibitors is essential. The present invention provides a highly purified protein farnesyltransferase which is effectively used in such a method to identify the specific inhibition of farnesyltransferase and to characterize the kinetic effects of inhibition on the enzyme.

A purified farnesyltransferase is required because use of a contaminated enzyme might obscure a true inhibitor, or lead to mischaracterization of an inhibitor.

The present invention provides a method for obtaining farnesyltransferase that is purified to near homogeneity. This method uses recombinant technology and includes the steps of constructing a yeast strain which overproduces farnesyltransferase. "Overproduction" is determined relative to the wild type yeast species comparable to the overproducing strain in other genetic aspects. "Overproduction" is also considered relative to the source yeast strains from which vectors, each containing one gene related to farnesyltransferase, are derived. That is, yeast have a certain low constitutive level of farnesyltransferase. Strains containing vectors each with the genes DPR1 or RAM2 have increased levels over the wild type levels of the order of about 5–10 fold. Synergism resulting from combining multiple copies of both DPR1 and RAM2 in a host yeast cell under the control of their own promoters produced unexpectedly high production. For example, 100-fold increases occurred. Even higher overproduction results when strong promoters replace the natural promoters. Embodiments of strong promoters include ADH for the DPR1 gene and GAP for the RAM2 gene.

An illustrative embodiment for a yeast host strain is *Saccharomyces cerevisiae*. Also suitable are Schizosaccharomyces species. More particularly, the host yeast strain is designated SP1 or UC100.

Embodiments of vectors used to transport genes related to farnesyltransferase production into host cells, are plasmids capable of transferring genes into yeast. Examples of such plasmids include YEpDPR1 and pBH28.

Many plasmids which contain genes related to farnesyltransferase production are transferred into host cells by methods known to those of skill in the art so that multiple copies of the genes are present in the host cells. Fifty copies of each gene or more are preferred, although greater or lesser number of copies are suitable depending on the circumstances and goals of a particular system. The gene sequences include either yeast or mammalian sequences with an promoter operable in a host cell.

Recombinant yeast cells are grown in suitable tissue culture medium. Suitable medium is that which facilitates optimum growth of the yeast while still permitting expression of genes to overproduce farnesyltransferase. An example of suitable medium is a synthetic medium lacking leucine and uracil so that selective markers based on these amino acids can be used to select recombanant cells. Medium in which yeast cells have been growing is termed "conditioned" medium.

Standard methods of yeast culture as described in Strathern et al., 1981 and Sherman et al., 1986 are suitable.

After the yeast cells have been growing in suitable medium for a period of time, the cells are collected by centrifugation. The cells are disrupted and then fractionated and the fractions are tested to identify those with farnesyltransferase activity. Ammonium sulfate fractionation is suitable for this purpose. Farnesyltransferase is then extracted from the identified supernatant fractions. Anion column chromatography is used to purify the protein farnesyltransferase. A high level of purity is achieved, that is, near homogeneity.

Mono Q column chromatography is an example of a suitable anion chromatography process. This method of purification has an advantage over methods used for purification of mammalian farnesyltransferase from rat brain, for example, which require use of a peptide affinity column for the last step of enzyme purification. It is advantageous to omit this step because it is difficult to replicate. Moreover, rat brains must be obtained.

The methods of the present invention result in the production for the first time of a highly purified yeast farnesyltransferase. The purified enzyme was found to have the following properties: it is a heterodimer having an estimated approximate molecular weight of 90 kDa. The heterodimer consists of two subunits. The estimated approximate molecular weights of the subunits are 43 kDa and 34 kDa, respectively. The optimum pH is 7.8. The optimum temperature is 50° C. As would be expected if the purified product is farnesyltransferase, the enzyme is inhibited by contact with a peptide containing at its C-terminal end, the sequence CAAX, wherein C designates cysteine, A designates an aliphatic amino acid, and X may be any amino acid.

The kinetic properties of the purified enzyme indicate a Km of 8.1 µM when tested against the substrate FPP, and a Km of 5.1 µM when tested against the substrate GST-CIIS.

One important use of purified farnesyltransferase is to identify and characterize potential inhibitors of farnesyltransferase. The purified enzyme is used to determine the specificity of the enzyme and to quantify the effects of the potential inhibitor on the specific activity and kinetics of farnesyltransferase.

An embodiment of a test for the inhibiting activity of farnesyltransferase is to measure the amount of [$^3$H] farnesyl transferred from [$^3$H] Fpp to the RAS2CT1 protein.

Using the methods disclosed herein, it was determined that inhibitors of farnesyltransferase are produced by strains of Streptomyces. One such inhibitor is manumycin, an antibiotic.

When inhibitors are used for chemotherapy, yeast recombinant technology is advantageous because drug resistant genes are likely to complicate treatment. Transformed yeast will produce an identifiable phenotype in these cases and mechanisms of resistance may be determined so that appropriate inhibition therapy may be developed.

DETAILED DESCRIPTION OF PREFERRED EMBODIMENTS

Figure 1:
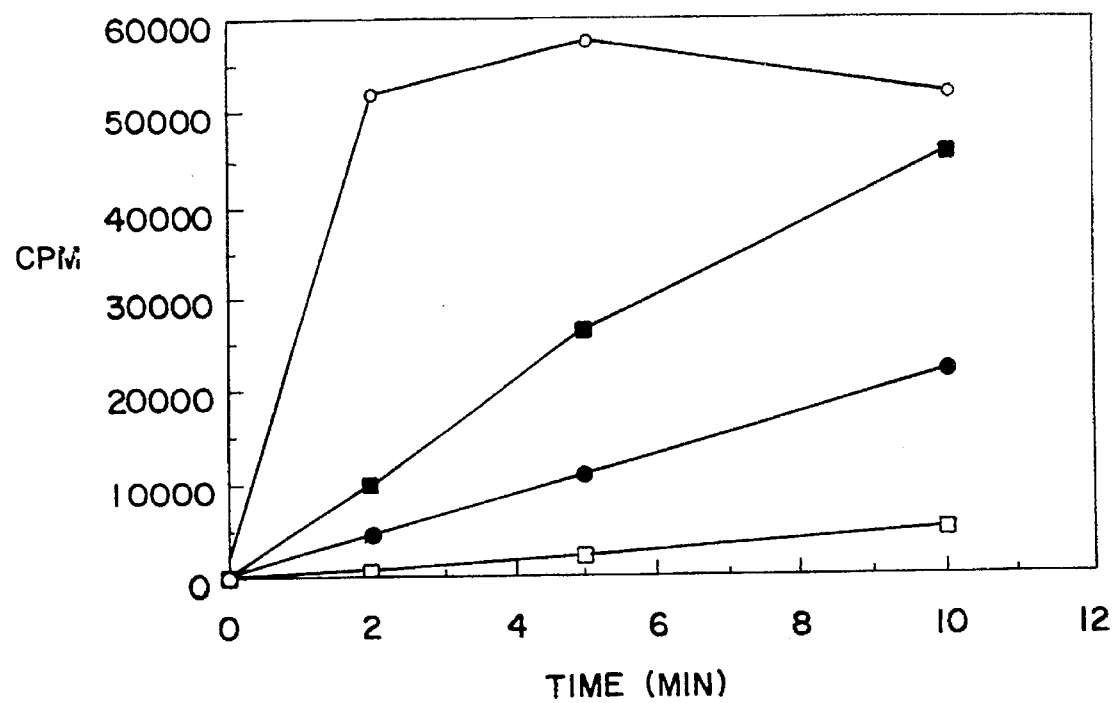
FIG. 1 Over production of FTase.

Although purified mammalian (FTase) was available from rat brains, a surrogate which would be readily available to test the specificity and kinetics of potential inhibitors of FTase was desirable. An aspect of the present invention was to find such a surrogate. Yeast FTase was selected as a possible surrogate, but because yeast FTase was not purified and characterized, its acceptability as a surrogate was conjectural. Therefore, an aspect of the invention was to purify yeast FTase. Overproduction of the enzyme in yeast was developed as a method to obtain large enough quantities of FTase to simplify its purification. This was achieved by incorporating multiple copies of two genes encoding for both subunits of the FTase into a host yeast cell. It was unexpected that synergistic production would result. Merely putting multiply copies of a gene into a host cell does not quarantee the overproduction of a particular gene product. The host cell machinery does not predictably response to insertion of a large number of plasmids carrying multiple copies of a gene or genes, by overproduction of a particular gene product. However, using the methods of the present invention, sufficient enzyme was overproduced such that purification was achieved. Characterization and use of the purified enzyme showed that indeed, yeast FTase was an acceptable surrogate for mammalian FTase. The use was to confirm the specificity and kinetics of potential inhibitors of FTase for use as chemotherapeutic agents. Recombinant yeast systems are also useful for determining the active site of FTase. Moreover, the method is applicable for overproduction and analysis of the mammalian enzyme by recombinant technology.

Protein farnesyltransferase (FTase) catalyses the addition of a farnesyl group to a cysteine within the so-called 'CAAX box' at the C-terminus of various proteins. Purification of *Saccharomyces cerevisiae* FTase to near homogeneity was accomplished by constructing a yeast strain which overproduces FTase approximately a 100-fold. The purified enzyme was a heterodimer of approximately 90 kDa and consisted of 43 kDa and 34 kDa subunits. The 43 kDa subunit was shown to be the product of the DPR1 gene by using an antibody raised against baculovirus-produced DPR1 polypeptide. The purified enzyme required $Mg^{2+}$, showed a pH optimum of 7.8 and was most active at 50° C. The $K_m$ values for farnesyl pyrophosphate (Fpp) and GST-CIIS protein of $K_m^{Fpp}$ 8.1 and $K_m^{GST-CIIS}$ of 5.1 µM respectively. The enzyme was capable of was farnesylating GST-CIIL (the same as GST-CIIS except the C-terminal serine is changed to leucine), a substrate protein for the enzyme geranylgeranyltransferase (GGTase)-CIIS although with a higher apparent $K_m$ than for GST-CIIS. Like its mammalian counterpart, yeast Ftase activity was inhibited by peptides containing the C-terminal CAAX sequence (that is where C=cysteine, one A=aliphatic amino acid and X=any amino acid). These results provide direct evidence that the yeast and mammalian FTase are structurally and functionally very similar.

Plasmid strains DNAs and peptides

SP1 (MATα leu2 trp1 his3 ade8 can1) (Toda et al., 1985) has been used for most experiments. Other *Saccharomyces cerevisiae* strains are RS16-4C (MATα ura3 trp1 ade8 can1 SUP84L) and UC100 (MATα leu2 trp1 ura3 pep4 prb) (Goodman et al., 1990). Cells were grown in synthetic media containing 2% glucose and lacking appropriate amino acids (Sherman et al., 1986). The plasmid YEpDPR1 contains 4.8 kbp BamHI to SalI region of DPR1 gene YEp24 (Tamanoi et al., 1988; Goodman et al., 1988), pBH28 (obtained from Scott Powers, Robert Wood Johnson Medical School, Piscataway, N.J., U.S.A.) contains the RAM2 gene on the multicopy plasmid YEp13. The RAM2 gene can be PCR amplified using appropriate oligonucleotide primers (He et al.,) and *Saccharomyces cerevisae* genomic DNA (YL1004b, Clontech Laboratories Inc., Palo Alto, Calif. 94303-43607). The gene can be placed into yeast plasmid such as YEp13. Synthetic peptides [MG13 SEQ ID NO: 2 (NSNSVCCTLM) MG14 SEQ ID NO: 3 (SGSGGCIIS) and P119 SEQ ID NO: 4 (YPYDVPDYAS)] were obtained from Malcolm Whiteway, NRC Biotechnology Research, Montreal, Canada. LHRH (luteinizing-hormone-releasing factor) peptide SEQ. ID NO: 5 (EHWSYGLRPG) was from Boeringer Mannheim (Cat. No. 253,197). pVL1392 and AcNPV DNAs were gifts from Max D. Summers (Texas A&M University, College Station, Tex. U.S.A. *Spodoptera frugiperda* Sf9 insect cells were from the American Type Culture Collection. (ATCC Accession No. CRL1711).

Prenyltransferase assays and preparation of crude extracts

Prenyltransferase assays were performed essentially as described in Goodman et al., 1990; Finegold et al., 1991. Briefly, the reaction mixture (20 µl) contained 50 mM potassium phosphate, pH 7.4 (or 50 mM Tris/HCl, pH 8.0), 10 mM$MgCl_2$, 5 mM DTT, 5 µM $ZnCl_2$, 0.8–1.12 µM [$^3$H] farnesyl pyrophosphate (Fpp) (20 Ci/mmol; New England Nuclear) or [$^3$H] geranylgeranyl pyrophosphate (GGpp) (20 Ci/mmol; New England Nuclear, Boston, Mass.), 19 µg of GST-CIIS or 30 µg of GST-CIIL protein and enzymes. Incubation was carried out at 37° C., and the radioactivity incorporated was determined by spotting the reaction mixture onto a filter paper, treating with 10% trichloroacetic acid, followed by ethanol and acetone washing. The variability between different FTase assay was generally within 8% of the values shown. For example, the values shown in FIGS. 1 and 4 had the variability of 7.2% and 5.1% respectively between different assays. Crude extracts of yeast cells were prepared by suspending cells in Buffer A (0.1M Mes-NaOH (pH 6.5 0.1 mM $MgCl_2$/0.1 mM EGTA/1 mM DTT) containing 2 mM phenylmethanesulphonyl fluoride (PMSF) and disrupting cells using glass beads. The extracts were centrifuged at 100,000 g for 1 h. after low-speed centrifugation. Protein concentrations of the crude extracts as determined by the bicinchoninic acid ("BCA") method (Smith et al., 1985) were approximately 10 mg/ml.

Purification and characterization of FTase

Yeast FTase was purified as follows. SP1 cells carrying YEpDPR1 and pBH28 plasmids were grown in a synthetic medium lacking leucine and uracil to late-exponential phase. A 20 g (wet weight) portion of cells was suspended in 60 ml of buffer A containing 3.1 µg/ml bestatin, 1 mMPMSF, 6.7 µg/ml pepstatin, 37 µg/ml tosyllysylchloromethane ('TLCK'), 35 µg/ml tosylphenylalanylchloromethane ('TPCK') and were disrupted with glass beads using a Bead Beater, (Biospec, Bartlesville, Okla.). After low-speed centrifugation at 1500 g for 10 min, crude soluble extracts were prepared by centrifuging at 100,000 g for 1 h. $(NH_4)_2SO_4$ was added to the extracts to make 30% saturation and the pellet was removed by centrifugation. Additional $(NH_4)_2SO_4$ was added to the supernatant to make 60% saturation, and the pellet was collected. The pellet was suspended in a small volume of 25 mM Tris-HCl (pH 7.4)1 1 mM DTT/0.1 mM $MgCl_2$/0.1 mM EGTA and was dialysed against the same buffer. The sample was applied to a Mono Q column (HR 16/10; Pharmacia, Piscataway, N.J.), and the elution was carried out with a salt gradient of 0.1–0.4M NaCl in Mono Q buffer consisting of 25 mM Tris-HCl (pH 7.4)/1 mM MgCl, and 1 mM DTT. The activity was eluted at a salt concentration of approximately 250 mM. The peak fractions were pooled, n-octyl β-D-glucopyranoside was added to 0.2%, and stored frozen at −80° C. When necessary, rechromatography on Mono Q (HR5/5) was carried out by diluting the pooled fractions with the Mono Q buffer and reapplying them to the column.

In some embodiments, the $(NH_4)_4SO_4$-fractionation step was replaced by an alternative step which involves DEAE-Sepharose followed by Sephacryl S-300. High-speed supernatants from 15 g of cells were applied on to DEAE-Sepharose CL-4B (Pharmacia) (column volume 130 ml) equilibrated with Mono Q buffer. Elution was carried out by increasing NaCl concentration from 0 to 0.4M. The peak fractions eluting with a salt concentration of 0.17M were concentrated by adding $(NH_4)_4SO_4$ to 80% saturation and were applied to a Sephacryl S-300 (column volume 100 ml) which had been equilibrated in 25 mM Tris/HCl (pH 7.4)/1 mM $MgCl_2$/50 mM NaCl. The peak fractions were pooled and applied to a Mono Q column (HR5/5).

Expression of DPR1 protein in baculovirus-infected insect cells and production of antibody, against DPR1 protein The polymerase chain reaction (PCR) was used to generate a DNA sequence containing the DPR1 coding sequence of YCpDPR2.4 (Goodman et al., 1988) and restriction sites suitable for subcloning into a baculovirus transfer vector. The primers used for PCR were 5'-GGGCCCGTC-GACTTAACTTGGAGAAGATAAATTGG-3' (SEQ. ID NO: 6) and 5'-CCCGGGGAATTCATGCGACAGAGAG-TAGGAAGG-3'(SEQ. ID NO: 7). The PCR product was treated with T4 DNA polymerase in the presence of dNTPs, digested with EcoR1 and ligated into the baculovirus transfer vector pVL1392, which had been digested with SmaI and EcoRI. The sequence of the junctions at the 5' and 3' end of the DPR1 gene was confirmed. The resulting plasmid, called pAcS13, was co-transfected along with DNA of strain E2 of *Autographa/californica* nuclear polyhedrosis virus (AcNPV) into *Spodoptera frugiperda* Sf9 insect cells and recombinant viruses were isolated as described in Summers and Smith, 1987.

Expression of DPR1 in the baculovirus system was accomplished by growing Sf9 cells at $1.5 \times 10^4$/ml in 50 ml or 500 ml of suspension cultures in Ex-Cell 400 medium (JHR Biosciences, Lenexa, Kans., U.S.A.) at 27° C. infected with recombinant viruses at a multiplicity of infection of 10. At 2 days after infection, the Sf9 cells were centrifuged at 100,000 g for 10 min, resuspended in ice-cold lysis buffer [10 mM Hepes (pH 7.4)/1 mM $MgCl_2$/1 mM EGTA/1 mM PMSF] at $4 \times 10^7$ cells/ml, homogenized with 20 strokes in a Dounce-type grinder with a 'B' pestle and centrifuged at 100,000 g for 1 h at 4° C. The supernatant, referred to as the 'S100 fraction', contained DPR1 protein as determined by Coomassie Blue staining of the SDS/polyacrylarmide gel.

The baculovirus-expressed DPR1 from the S100 fraction was partially purified as follows. The S100 fraction was applied to a DE52 column equilibrated in 20 mMTris/HCl (pH 7.4)/1 mMDTT/5% glycerol/0.1mMEDTA/0.5 mM PMSF. Elution was carried out by increasing NaCl concentration from 0 to 0.6M. DPR1 polypeptide, as determined by SDS/PAGE, was eluted with 0.16M NaCl and was completely separated from insect-cell FTase, which was eluted by 0.2M NaCl. The DPR1 peak fractions were pooled, concentrated and loaded on to a Sephacryl S200 HR column using 50 mM sodium phosphate (pH 7.0)1 mMDTT/200 mM NaCl/5% glycerol as a buffer. The fractions containing the peak of DPR1 were pooled and further purified by a preparative SDS/PAGE. The region of the gel containing DPR1 was excised and the protein recovered from the gel was used to immunize rabbits. Immunoblot detection of DPR1 polypeptide was carried out by transferring proteins to nitrocellulose membranes, incubating them with the anti-DPR1 serum, and detecting the bound antibody by a biotinylated antibody to rabbit immunoglobulin and an avidin-horseradish peroxidase complex (Vectastain ABC kit, Vector Laboratories) as described by Finegold et al. (1990).

Overexpression of DPR1 and RAM2 results in a dramatic increase of FTase activity, The DPR1 gene has been cloned. The gene encodes a protein of 431 residues and the cell-free translation product migrates as a protein of approximately 43 kDa (Goodman et al., 1988). The Ram2 gene encodes a protein of 316 amino acid residues (He et al., 1991). These two genes were placed on multicopy plasmids and transfected into wild-type yeast cells, either together or individually. Extracts of SP1 cells carrying pBH28 and YEpDPR1(○), pBH28 and YEp24(●), YEp13 and YEpDPR1(■), YEp13 and YEp24(□) as shown in FIG. 1 were prepared and FTase activity was assayed as described herein. 50 μg of the extracts were used per 60 μl reaction mixture and 10 μl aliquots were removed from the reaction mixture after incubating 2, 5 and 10 minutes and the incorporation of the radioactivity was determined as described herein. As FIG. 1 shows, extracts of cells carrying both DPR1 and RAM2 plasmids exhibited a significantly higher level of FTase activity compared with the cells carrying the vectors. Comparison of the rate of the reaction suggested that the overexpressor has approximately 100-fold higher FTase activity. In contrast, overexpression of DPR1 alone resulted in an approximately 10-fold increase in activity. Similarly, overexpression of RAM2 alone resulted in a 6-fold increase. Thus, both genes are needed to obtain the highest level of FTase activity. The slight increase of the activity seen with single overexpressors could be due to the presence of free subunits in these cells. Essentially similar results were obtained when overexpression of DPR1 and/or RAM2 genes was carried out in another yeast strain, UC100; a significant increase of FTase activity was seen only when both DPR1 and RAM2 were expressed.

Purification of FTase

Increased FTase activity in the overexpresser provided an excellent source to purify FTase. Extracts of the cells overexpressing both DPR1 and RAM2 were subjected to $(NH_4)_2SO_4$ fractionation followed by Mono Q column chromatography. The FTase activity was eluted at a salt concentration of approximately 250 mM. Occasionally the activity was split into two peaks. Analysis by SDS/PAGE did not reveal any differences between the two peaks. Both contained two bands. FTase was purified from 20 g of SP1 cells carrying pBH28 and YEpDPR1 plasmids as described herein. FTase activity of each fraction was determined as described herein. A unit of enzyme activity is defined as the amount of enzyme required to transfer 1 pmol of [$^3$H] farnesyl from [$^3$H] Fpp into acid-insoluble materials in 1 min at 37° C. As shown in Table 1, this scheme resulted in 3108-fold purification of the enzyme activity, with 73% recovery. The enzyme kept frozen at −80° C. in the presence of a noctyl β-D-glucopyranoside was stable for at least two months.

TABLE 1

| | Purification of FTase | | | | |
|---|---|---|---|---|---|
| | Protein (mg) | Total activity (units) | Specific activity (units/mg) | Recovery (%) | Purification (fold) |
| High-speed supernatant | 675 | 51030 | 76 | 100 | 1 |
| $(NH_4)_2SO_4$ | 57 | 36879 | 647 | 72 | 8.6 |
| Mono Q | 0.16 | 37051 | 234975 | 73 | 3108 |

Molecular mass and subunits

A Superose 12 column profile was made of the FTase activity. FTase purified from SP1 cells carrying pBH28 and YEpDPR1 was applied onto Superose 12 column which had been equilibrated with 25 mM Tris-HCl (pH 7.4), 50 mM NaCl, 1 mM DTT, 1 mM $MgCl_2$. FTase was eluted using the above buffer. Markers used were Blue Dextran (2000 kDa), alcohol dehydrogenase (150 kDa), bovine serum albumin (69 kDa) and carbonic anhydrase (29 kDa). A single peak of activity was observed that was eluted in fractions corresponding to proteins of 80–100 kDa. Comparison with the marker proteins suggested that the native molecular mass of the yeast FTase is approximately 90 kDa.

FTase was purified from SP1 cells carrying plasmids pBH28 and YEpDPR1 as described herein. The FTase was analyzed on a 12.5% SDS polyacrylamide gel and silver stained. Marker proteins used are bovine serum albumin (69 kDa), ovalbumin (46 kDa), glyceraldehyde-3-phosphate dehydrogenase (36 kDa), carbonic anhydrase (29 kDa), trypsin inhibitor (20 kDa) and α-lactalbumin (14 kDa). SDS/PAGE of the purified FTase revealed the presence of two major bands. The two bands corresponded to proteins having apparent molecular masses of 43 and 34 kDa. The bands seen at 60 kDa were present even in lanes only containing sample buffer and thus appear to represent keratins, common artifacts of silver staining (Ochs et al., 1983). To demonstrate that the 43 and 34 kDa bands represented polypeptides associated with the FTase activity, the sample was applied to a Superose 12 column and the column fractions were analyzed by SDS/PAGE. FTase purified from SP1 cells carrying pBH28 and YEpDPR1 was applied onto Superose 12 column. The two bands were detected in the fractions where the FTase activity was detected. Co-elution of these two bands with the FTase activity was also seen when the sample was analyzed by means of a Mono Q column. Thus, the yeast FTase consists of two polypeptides of molecular mass 43 and 34 kDa.

Effects of pH and temperature on FTase activity

Effect of pH on enzyme activity was examined from pH 3–10 using citrate/phosphate, phosphate, ammediol and Tris/HCl buffers. Incubations were carried out for 10 minutes at 37° C. and the radioactivity incorporated was measured as described herein. A broad pH optimum between 7 and 9 was observed. Results with Tris/HCl buffer, demonstrated that the maximum activity was obtained at pH 7.8.

The temperature-dependence of the enzyme activity profile showed the enzyme was highly active above 37° C. Little activity was detected below 24° C. Incubations were carried out for 10 minutes at the indicated temperature and the radioactivity incorporated was measured as described herein. The activity increased up to 50° C. and rapidly decreased above 55° C. Preincubation of the FTase at 55° C. for 10 min resulted in 88% decrease of the activity. The presence of Fpp during the preincubation reduced this decrease to 67% of that of untreated enzyme. In contrast, addition of GST-CIIS protein during the preincubation did not have any significant effect.

Effects of bivalent and univalent cations

Figure 2:
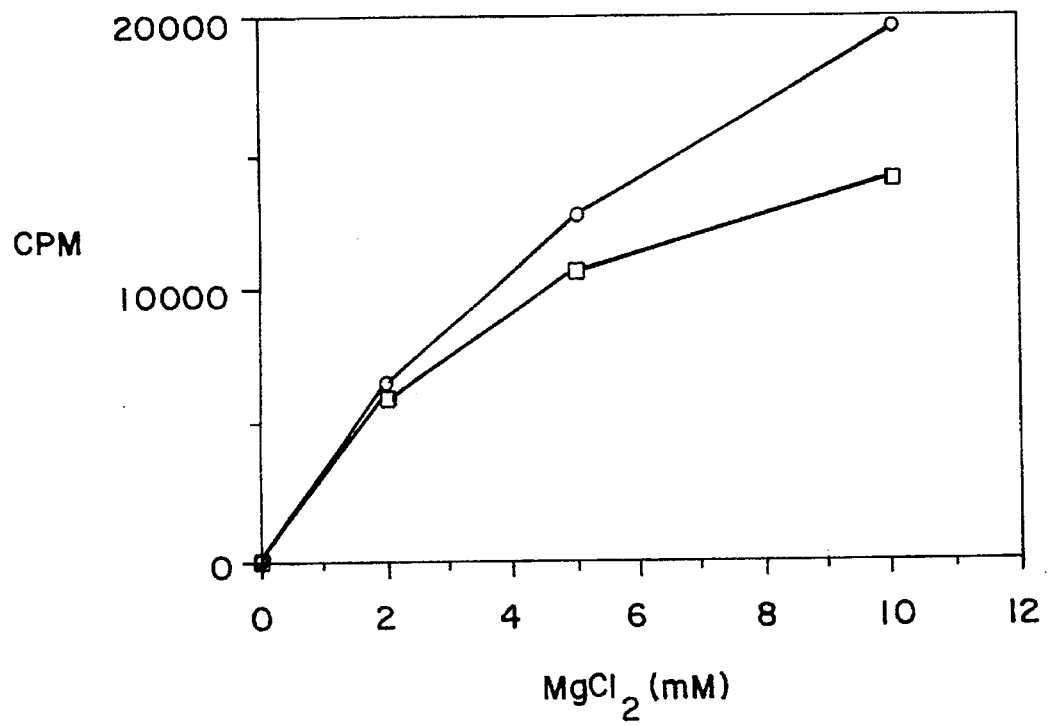
FIG. 2 Divalent cation requirement for FTase.

Addition of salts inhibited the FTase activity. Approximately 50% inhibition was seen with 100 mM NaCl, LiCl or KCl. Of the three, KCl showed the most inhibitory effect. The enzyme showed absolute requirement for bivalent cations. EDTA addition resulted in a dramatic inhibition of the FTase activity. Addition of 5 mM $Mg^{2+}$ to the EDTA-inhibited enzyme fully restored the activity. Further addition of zinc resulted in a slight increase of the activity (FIG. 2). Reaction mixture (20 µl) for results shown in open squares contained 1.12 µM [$^3$H] Fpp, 4.38 ng FTase, 19 µM GST-CIIS, 0.1 mM EDTA and the indicated concentration of $MgCl_2$. Reaction mixtures (20 µl) for results shown in closed diamond contained 0.1 mM $ZnCl_2$ in addition to the above. Incubation was carried out for 10 minutes at 37° C. and radioactivity incorporated was determined as described herein. Addition of 0.5–1 mM zinc alone was partially effective in the recovery of the activity of EDTA-treated enzyme; zinc alone recovered approximately 50% of the activity obtained with $Mg^{++}$ alone.

Substrate specificity

Figure 3:
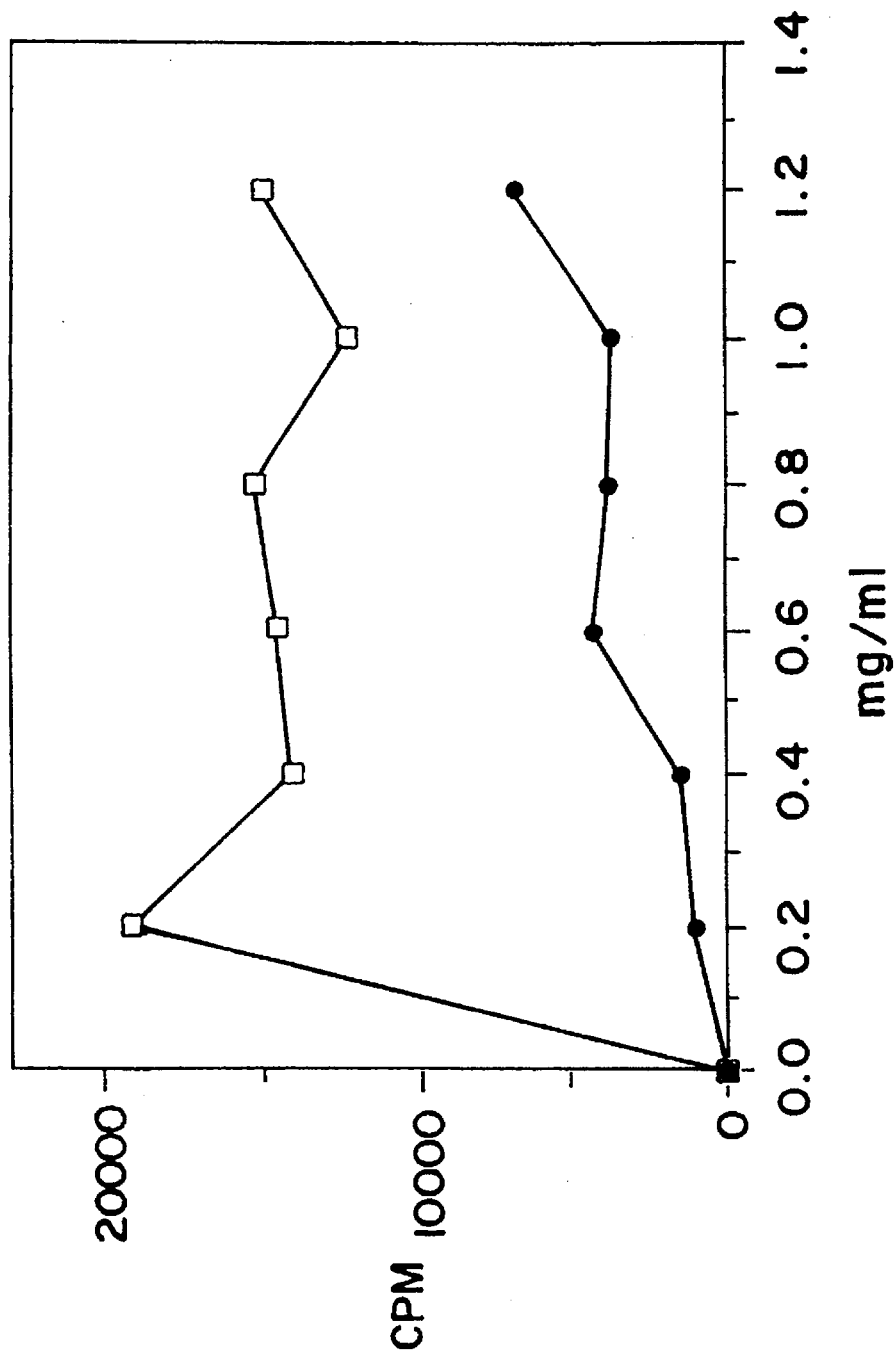
FIG. 3 Incorporation of Fpp into two different substrate proteins, GST-CIIS or GST-CIIL.

Substrate specificity of yeast FTase was investigated by comparing incorporation of Fpp or GGpp into two different substrate proteins, GST-CIIS (□) and GST-CIIL (●). GST-CIIL was previously shown to be an efficient substrate from GGTase (Finegold et al., 1991). Fpp was efficiently incorporated into GST-CIIS protein, whereas the incorporation of Fpp into GST-CIIL protein was much less efficient (FIG. 3). The reaction mixture (20 µl) contained 1.12 µM [$^3$H] Fpp, 20 ng FTase, and the indicated concentrations of either GST-CIIS or GST-CIIL1 protein. Incubations were carried out for 10 minutes at 37° C. and the radioactivity incorporated was measured as described herein.

Figure 4A:
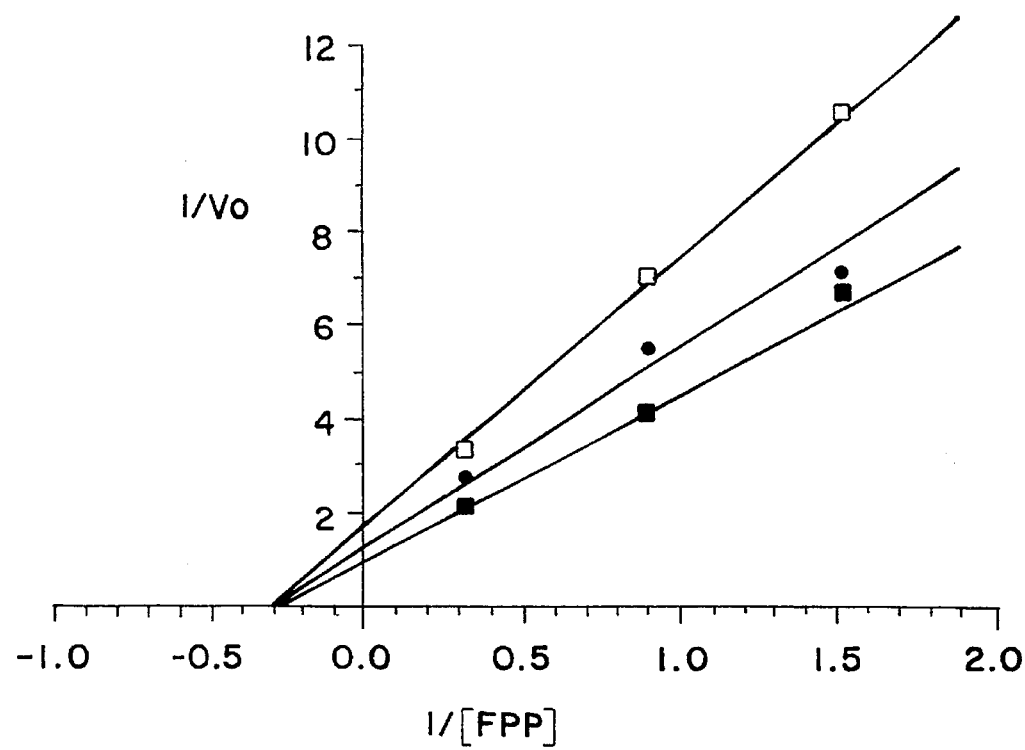
FIG. 4 Double reciprocal plots (Lineweaver-Burk), Panel A: The reaction mixture (20 µl) contained varying concentrations in µM of [$^3$H] Fpp, 20 ng FTase, and either 0.8 mg/ml (■), 0.3 mg/ml (♦) or 0.2 mg/ml (□) of GST-CIIS protein (29 kDa). Velocity was measured in pmol per minute. Panel B: The reaction mixture (20 µl) contained varying concentrations in mg/ml of GST-CIIS protein, 20 ng FTase, and either 3.3 µm (■), 1.1 µM (♦), or 0.66 µM (□) of [$^3$H] Fpp. Velocity was measured in pmol per minute. These experiments have been repeated three more times with similar results.
Figure 4B:
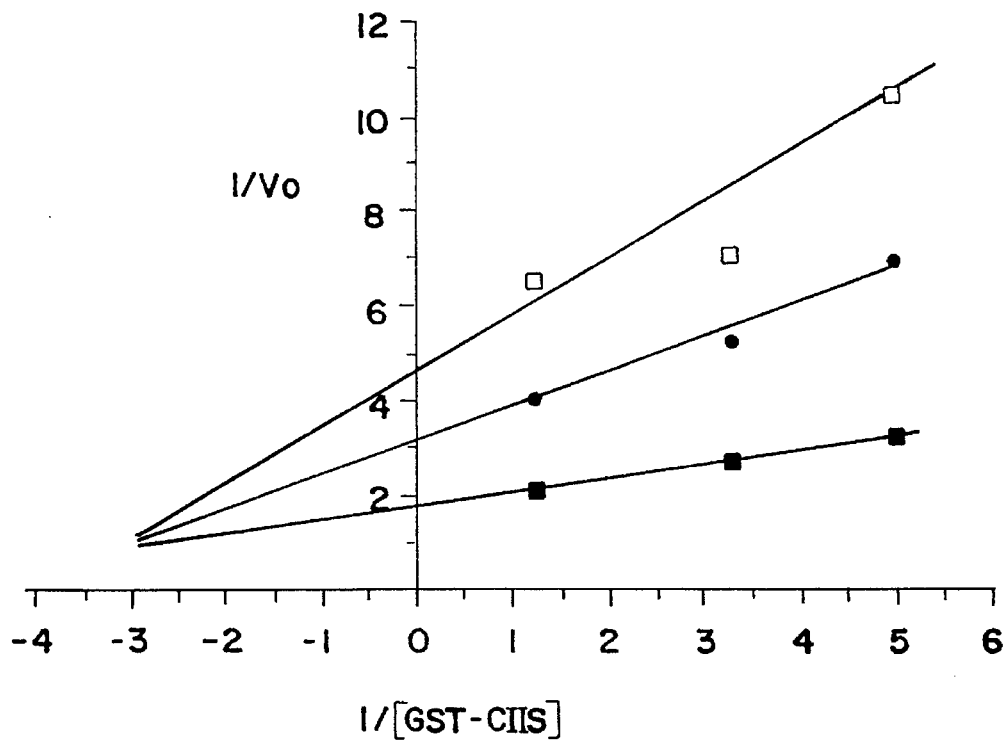

Surprisingly, however, a significant level of Fpp incorporation was seen with GST-CIIL protein at high GST-CIIL concentrations. An apparent $K_m$ obtained for GST-CIIL protein was 39 µM at Fpp concentration of 1.1 µM. Virtually no incorporation of GGpp was seen with either substrate protein. Effects of changing concentration of substrates, Fpp and GST-CIIS protein, are shown in FIG. 4. These experiments have been repeated three more times with similar results. Secondary plots from these plots, showed the $K_m$ Fpp and $K_m^{GTS-CHS}$ to be 8.1 and 5.1 µM respectively.

Peptide inhibition

Figure 5:
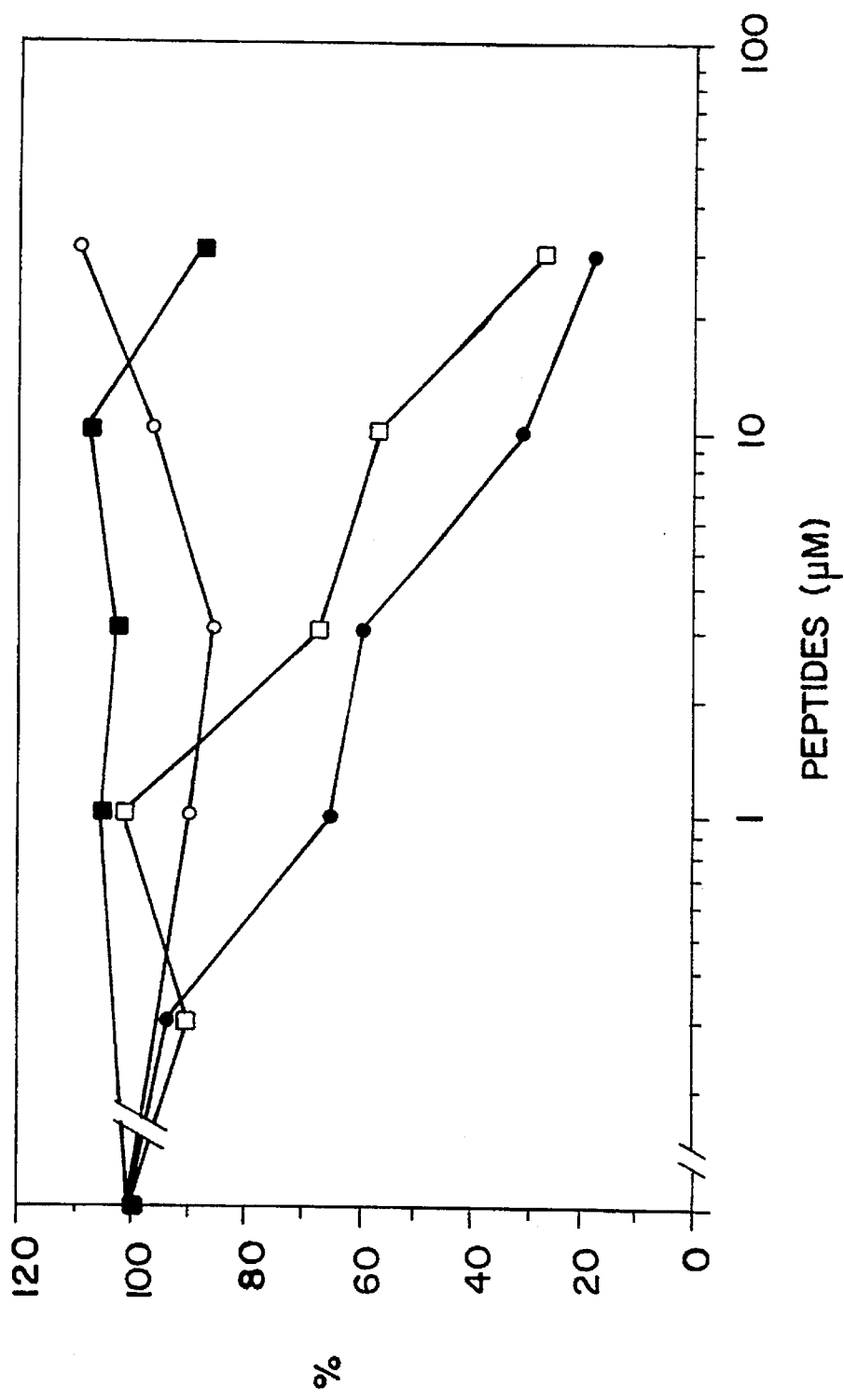
FIG. 5 Inhibition of FTase Activity by peptides.

Like its mammalian counterpart, the yeast FTase activity was strongly inhibited by the addition of peptides having a C-terminal CAAX sequence. As FIG. 5 shows, each reaction mixture (20 µl) contained 1.12 µM [$^3$H]Fpp, 4.38 ng FTase, 19 µg GST-CIIS and the indicated concentration of synthetic peptides MG13, MG14, P119 or LHRH. Dilution of the peptides was made in 10 mM DTT. Incubation was carried out for 10 minutes at 37° C. and the radioactivity incorporated was determined as described herein. The 100% value corresponds to 51,752 cpm as determined by carrying out the above reaction without peptides. The activity was inhibited by the addition of a peptide, MG14, which contained ten residues of RAS2 C-terminal sequence (SEQ ID NO: 3 SGSGGCCIIS; 50% inhibition was seen with 4 µM peptide (♦). Another peptide, MG13□, which contained ten residues of STE18 C-terminal sequence, (SEQ ID NO: 2) NSNSVC-CTLM, also inhibited FTase, with 50% inhibition observed in the presence of 10 µM peptide. By contrast, little inhibition was seen with two control peptides of the same size, P119 (■) and LHRH(◊), having unrelated sequences.

Production of antibody against DPR1 protein and identification of 43 kDa protein as DPR1 gene product Polyclonal antibody was raised against baculovirus-produced DPR1 protein. To accomplish this, DPR1 protein was first expressed in baculovirus-infected insect cells as described herein. Extracts were made, then cleared by a high-speed centrifugation. 32 µg of extracts prepared from Sf9 cells infected with the recombinant virus carrying the DPR1 gene or the control virus were analyzed on a 12.5% SDS polyacrylamide gel. The resulting supernatant was analyzed by SDS/PAGE. A prominent band of approximately 43 kDa was observed in Coomassie Blue-stained gels in S100 fraction derived from Sf9 cells infected with the recombinant viruses. This band was not present in the S100 fraction derived from cells infected with the control viruses.

DPR1 protein was separated from the insect cell FTase by DE52 cellulose column chromatography, because it was eluted from the column at a lower salt concentration than was FTase. The DPR1 protein, thus purified, was used to immunize rabbits to produce polyclonal antibody against DPR1. The antibody was identified by immunoblotting.

The rabbit sera containing the DPR1 antibody was used to probe the purified yeast FTase. A band corresponding to 43 kDa was detected by immunoblotting of the purified yeast FTase with the anti-DPR1 antibody. 0.57 μg and 1 μg of FTase as well as 2.3 μg of DPR1 polypeptide purified from baculovirus infected Sf9 cells were electrophoresed on a 12.5% SDS polyacrylamide gel, transferred to nitrocellulose membrane and probed with anti-DPR1 antibody as described herein. This band comigrated with the DPR1 protein purified from baculovirus-infected cells. The 34 kDa band, in contrast, did not cross-react with the DPR1 antibody. Thus the 43 kDa polypeptide is the product of the DPR1 gene. The antibody did not neutralize FTase activity, nor did it precipitate the activity.

Characterization of Yeast FTase

The purified yeast FTase is a heterodimer of approximately 90 kDa and consists of 43 kDa and 34 kDa subunits. By using an antibody directed against DPR1 it was shown that the 43 kDa polypeptide is the product of the DPR1 gene. The 34 kDa polypeptide is most likely to be the product of the RAM2 gene, since the RAM2 gene encodes a protein of 316 amino acid residues (He et al., 1991). A possible structure of this enzyme has been proposed previously, on the basis of the following observations: (i) mutations in either the DPR1 or RAM2 gene almost completely abolish FTase activity (Goodman et al., 1990; Schafer et al., 1990); (ii) DPR1 protein purified from *E. coli* can reconstitute FTase when added to the extracts prepared from dpr1 mutant cells; (iii) sequences of DPR1 and RAM2 proteins share a low, but significant, similarity with β- and α-subunits respectively of the mammalian FTase (Kobe et al., 1991; Chen et al., 1991); (iv) extracts of *E. coli* cells expressing both DPR1 and RAM2 exhibit FTase activity. What has been lacking in these studies is the direct demonstration of the structure of yeast FTase.

The methods of the present invention have permitted the first purification of the yeast FTase to an extent which demonstrates its structure and firmly establishes that the yeast FTase consists of the DPR1 and RAM2 gene products. This enzyme is indistinguishable from the enzyme purified from the non-overproducer yeast. This point was addressed by carrying out purification of FTase from yeast cells which had not been transformed with overexpression plasmids. FTase activity from these cells eluted as a single peak from a Mono Q column with a salt concentration of approximately 250 mM which was the same salt concentration that was used for the preparation from the overproducer. This enzyme had an apparent native molecular mass of 80–100 kDa as determined by Superose 12 column chromatography. The enzyme bound to a column containing a CAAX sequence, (SEQ ID NO: 8) GTPRASNRSCAIS. Elution of the enzyme from this column by changing the pH to 5 resulted in the appearance of two prominent bands having apparent molecular masses of 43 and 34 kDa. In addition, there are similarities between the overproduced enzyme and non-overproduced enzyme in their properties such as pH optimum, $Mg^{++}$ requirement and optimum temperature.

The yeast FTase continued to be active up to 50° C., but rapidly decreased in activity above 55° C. One possible explanation for the temperature-dependence curve not being bell-shaped could be alterations in the physical properties of the substrates, Fpp and GST-CIIS. Preincubation at 55° C. inactivated the FTase activity, but partial protection could be achieved by the addition of Fpp. On the other hand, the FTase was sensitive to the addition of salts. Another intriguing characteristic of the yeast FTase is its ability to utilize a GGTase substrate, GST-CIIL protein, albeit at a reduced efficiency. A similar observation was made with the mammalian FTase purified from porcine brain. Yokoyama et al. (1991) reported similar findings using the mammalian FTase and peptide substrates. Thus changing the C-terminal amino acid of a FTase substrate to leucine alters the substrate to be preferentially utilized by GGTase, but does not exclude it being used as a FTase substrate. This point may have to be taken into consideration when interpreting results of experiments looking at the effects of changing C-terminus of ras proteins to leucine.

Purification and characterization of the yeast FTase strongly suggest that the yeast enzyme is very similar to its mammalian counterpart. First, their physical structure appears to be similar. Both the mammalian and yeast enzymes are heterodimers of approximately 100 kDa. Furthermore, both enzymes are eluted from the Mono Q column by a very similar salt concentration, suggesting their similar overall charge. In addition, both enzymes have strong affinity for the CAAX sequence. Peptides containing C-terminal ten residues of RAS2 or STE18 inhibit yeast FTase activity. These results suggest strong evolutionary conservation of the FTase enzymes.

In summary, yeast FTase is a heterodimer consisting of DPR1 and RAM2 subunits. Because there are mutants of DPR1 and RAM2 already available and because more mutants can be generated by yeast genetics, the yeast system provides a suitable system to carry out a structure-function study of FTase.

EXAMPLE 1

Use of Purified Yeast PFTAse to Identify and Characterize Inhibitors of Farnesyltransferase.

A microbial screen was used in which inhibitors of farnesylation could be detected to screen microorganisms, isolated from soil and plants, for their ability to produce inhibitory compounds. Inhibitors were detected by their ability to restore the growth of the gpa/mutant (Schafer et al. 1989; Finegold et al. 1990). As a result of this screening, a culture of newly isolated Streptomyces was found to produce active compounds designated UCF1. Isolation and structural characterization of these active compounds assigned them to the manumycin family of antibiotics and resulted in the identification of two new compounds. The effect of these compounds on ras FTase and ras-activated murine tumors was determined. UCF1 is the first inhibitor of PFT exhibiting anti-tumor activity in vivo.

Materials. [1-$^3$H(N)]farnesyl pyrophosphate (Fpp) (20Ci/mmol, 1Ci=37GBq) and [1-$^3$H(N)]geranylgeranyl pyrophosphate (GGpp) (20Ci/mmol) were obtained from DuPont/NEN. RAS2CT1 protein is a truncated form of yeast RAS2 protein. The C-terminal sequence (SEQ ID NO: 9) CysIleIleSer is added to the C-terminus. GST-CIIL is a glutathione S-transferase fusion protein ending with C-terminal CysIleIleLeu sequence (SEQ ID NO: 10). *Saccharomyces cerevisiae* $K_m$g4-8c (MATα ura3 his3 trp1 leu2 gpa1::HIS3) carried a plasmid PG1501 containing the GPA1 gene controlled by GAL1 promoter.

Suppression of the lethality of gpa1 disruption. The yeast strain KMG4-SC carrying a plasmid pG1501 was grown at 30° C. to stationary phase in galactose medium. Agar plates were prepared by adding 50 μl of the above culture to 50 ml of glucose agar. Paper disks, soaked in drugs, were placed on the glucose agar plates and the plates were incubated at 30° C. for 3 days, and the diameters of the zones of growth were measured.

Farnesyltransferase assay. FTase from S. cerevisiae was purified from yeast cells overexpressing DPR1 and RAM2 as described herein. Rat brain FTase was partially purified by the method described by Reiss et al. PGGT purified from bovine brain was a gift of Drs. M. Gelb and K. Yokoyama (Univ. of Washington). FTase assays were carried out using RAS2CT1 protein and [$^3$H]Fpp according to the method described herein except that Tris-HCl(pH8) was used instead of phosphate buffer. PGGT assays were carried out using GST-CIIL protein and [$^3$H]GGpp as described herein except that Tris-HCl(pH7.4) was used instead of phosphate buffer. Since UCF1 was found to be inactivated by thiol, transferase assays were performed in the absence of dithiothreitol. Incubation was carried out at 37° C.

Anti-tumor activity. The K-BALB isograft line was established by subcutaneous inoculation of the cultured Ki-ras-transformed murine fibrosarcoma cells into adult male BALB/c mice weighing 20 to 25 g obtained from Japan Charles River Co., Atsugi, Japan. The HT1080 xenograft line was established by subcutaneous inoculation of cultured human fibrosarcoma HT1080 into adult male BALB/c-nu/nu mice weighing 23 to 27 g obtained from Nippon Clea Co., Tokyo, Japan. For evaluation of anti-tumor activity, tumor volume was calculated according to the method of the National Cancer Institute. Drug efficacy was expressed as the percentage of the mean V/Vo value against that of the control group, were V is the tumor volume at the day of evaluation and Vo is the tumor volume at the day of the initial treatment with the drug. Drugs were administered intraperitoneally daily for 5 days from Day 0 to Day 4. Murine fibrosarcoma K-BALB and human fibrosarcoma HT1080 were transplanted on Day 5. Statistical analysis was done by Student's t test (2-tailed).

Figure 6A:
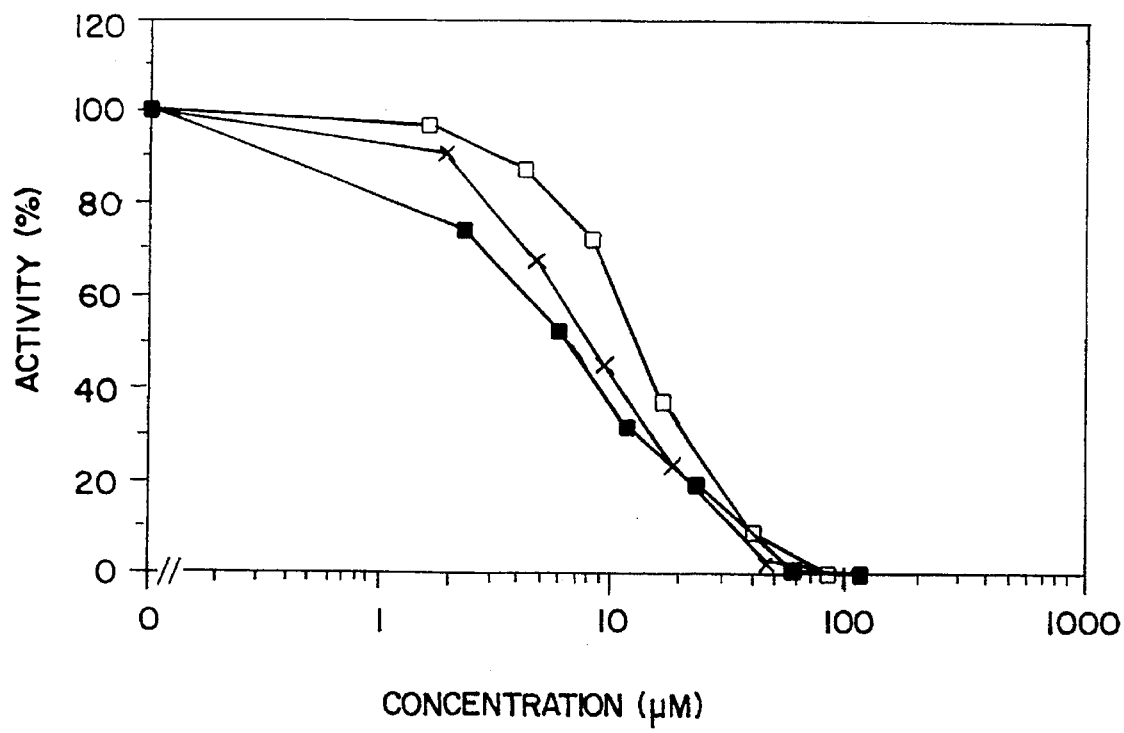
FIG. 6A Inhibition of yeast FTase by UCF1.
Figure 6B:
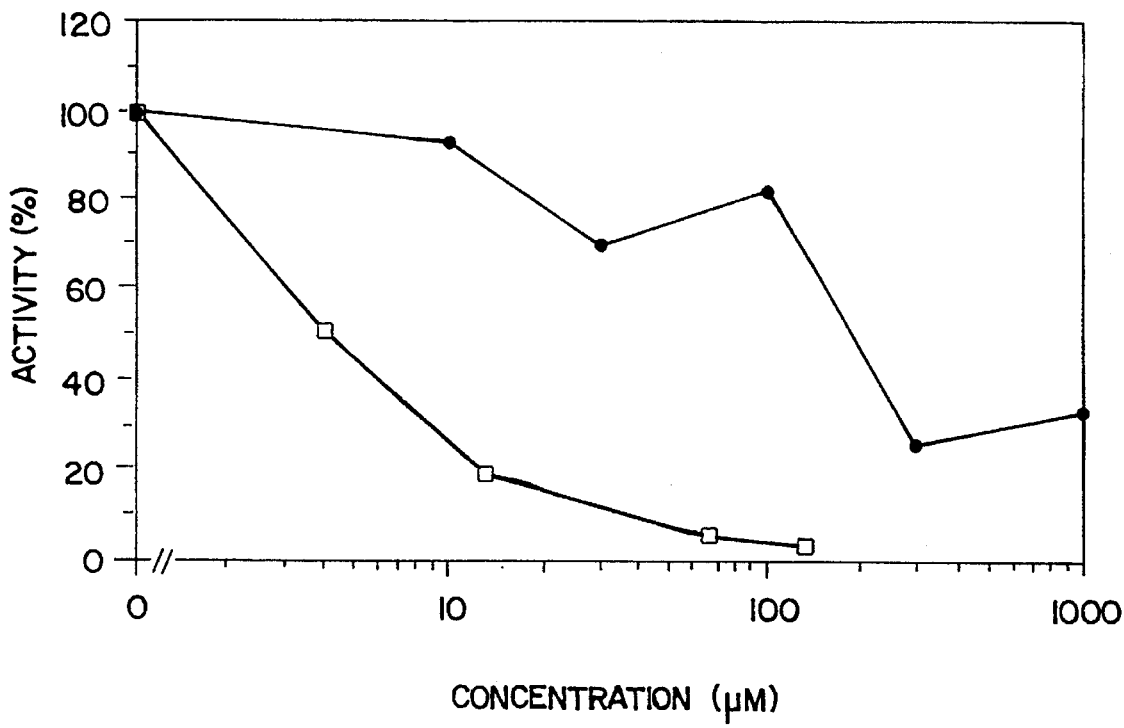
FIG. 6B Inhibition of PGGTI and FTase by UCF1-C.

Inhibition of Farnesyltransferase. The effect of UCF1 on PFT activity is shown in FIG. 6A and 6B. As can be seen, UCF1-A, UCF1-B, and UCF1-C all inhibited the activity of yeast PFT in a concentration dependent manner. Among these compounds, UCF1-C(■) showed the strongest activity. The $IC_{50}$ value for UCF1-C in this experiment was 5 μM whereas the $IC_{50}$ values for UCF1-A and UCF1-B were 13 (■) and 7 μM (x), respectively.

Results

FIG. 6B compares the effect of UCF1-C on PGGT I and PFT. As can be seen, UCF1-C is much less efficient in inhibiting PGGT I. The $IC_{50}$ value for PGGT I inhibition is 180 μM and approximately 30% of the activity is still detectable even at 1 mM concentration. Thus, UCF1-C appears to preferentially inhibit PFT.

Figure 7A:
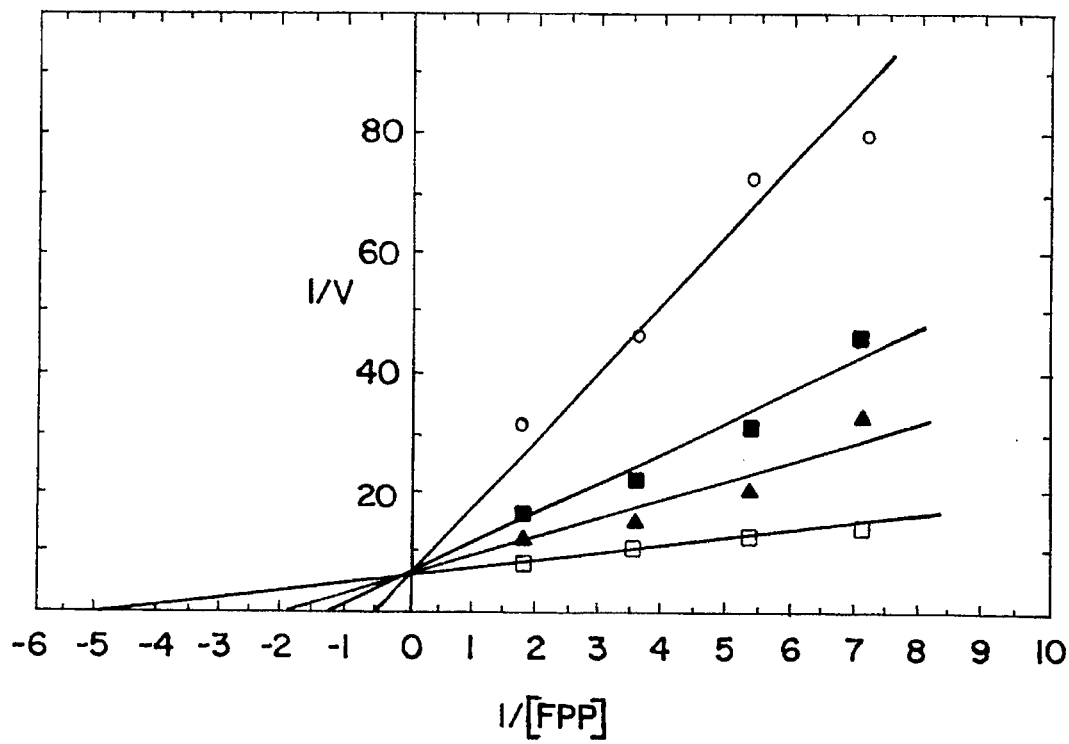
FIG. 7A Effect of UCF1-C on the kinetics of FTase with respect to the substrate Fpp.
Figure 7B:
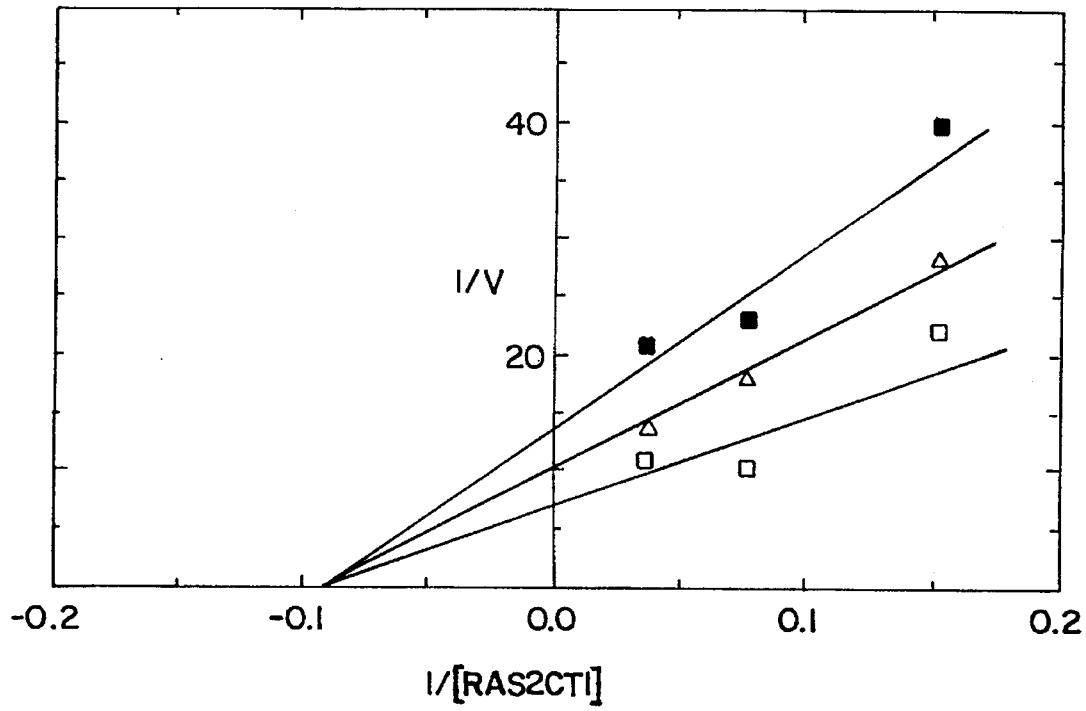
FIG. 7B Effect of UCF1-C on the kinetics of FTase with respect to the substrate ras.

To investigate the mechanism of inhibition by UCF1-C, kinetic analyses were carried out. FIG. 7A shows a Lineweaver-Burk plot of PFT using various concentrations of Fpp and UCF1-C (□=0 μM, ▲=10 μM, ■=20 μM, and o=40 μM) and a constant concentration of ras. As can be seen, the addition of UCF1-C changes the Km value for Fpp but does not change Vmax, suggesting that UCF1-C is a competitive inhibitor of Fpp. A secondary plot derived by plotting slopes against UCF1-C concentration gave the Ki value of 1.2 μM. In contrast to this, UCF1-C does not appear to affect the Km value for the substrate protein, RAS2. This is shown in FIG. 7B. The same Km value was observed when the Lineweaver-Burke plot was analyzed under different ras and UCF1-C concentrations (□=0 μM, ▲=10 μM, and ■=20 μM) in the presence of a constant concentration of Fpp. Thus, UCF1-C appears to act as a competitive inhibitor of PFT with respect to Fpp and a non-competitive inhibitor with respect to ras protein.

EXAMPLE 2

Use of Recombinant Yeast to Determine the Active Site of FTase (A) Generation of UCF1 Resistant FTase.

UCF1 is an Inhibitor of yeast FTase (see Example 1). When yeast FTase is defective, yeast cells show distinct phenotypes such as temperature sensitive growth and sterility specific to MATa cells. Addition of a drug to be tested to the growing yeast cells at an appropriate concentration results in the temperature sensitive growth.

The above phenotypes seen with yeast enable the isolation of UCF1 resistant yeast strains. Briefly, yeast MATa cells are mutagenized with ethylmethane sulfonate and subjected to the drug treatment of 37° C. The drug resistant colonies grown at this temperature are isolated. They are further screened for the sterility in the presence of the drug. FTase from these cells is examined to see whether the enzyme is resistant to the drug.

An alternative procedure is to randomly mutagenize the FTase genes, DPR1 and RAM2. This can be accomplished using various methods such as PCR amplification in the presence of Mn, or limited elongation followed by misincorporation of deoxynucleotides. The mutagenized genes are transformed into wild type MATa yeast cells and the drug resistant cells are isolated as above.

The method outlined here is not limited to the isolation of UCF1 resistant FTase. Drugs other than UCF1 can also be tested.

(B) Characterization of Drug Resistant FTase.

Ftase from the drug treatment cells is purified and characterized. The characterization includes binding of FPP and ras proteins, as well as interaction between the two subunits. Kinetic of the FTase reaction are investigated.

In addition, DPR1 and RAM2 genes are isolated from the drug resistant cells, and their sequences are determined. Site of the mutations on FTase amino acid sequence is determined.

(C) Significance

The information obtained will provide information about the organization of the active site of FTase. UCF1 is a competitive inhibitor of Fpp, the information concerning the FPP binding site will be obtained. Determination of amino acids altered in the drug resistant FTase will provide useful information regarding which amino acid residues are involved in the substrate binding and the catalysis.

The above results will provide useful information concerning the design of drugs which inhibit FTase. Various versions of the inhibitors based on those already found as well as new drugs need to be designed. These are needed to develop effective anti-cancer drugs.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

Cys  Xaa  Xaa  Xaa
  1

( 2 ) INFORMATION FOR SEQ ID NO:2:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

Asn  Ser  Asn  Ser  Val  Cys  Cys  Thr  Leu  Met
  1                   5                        10

( 2 ) INFORMATION FOR SEQ ID NO:3:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Ser  Gly  Ser  Gly  Gly  Cys  Cys  Ile  Ile  Ser
  1                   5                        10

( 2 ) INFORMATION FOR SEQ ID NO:4:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Tyr  Pro  Tyr  Asp  Val  Pro  Asp  Tyr  Ala  Ser
  1                   5                        10

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Glu His Trp Ser Tyr Gly Leu Arg Pro Gly
1               5                   10

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGGCCCGTCG ACTTAACTTG GAGAAGATAA ATTGG                     35

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CCCGGGGAAT TCATGCGACA GAGAGTAGGA AGG                       33

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Gly Thr Pro Arg Ala Ser Asn Arg Ser Cys Ala Ile Ser
1               5                   10

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Cys Ile Ile Ser
1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Cys  Ile  Ile  Leu
1
```

The references listed below are incorporated herein by reference to the extent that they supplement, explain, provide a background for, or teach methodology, techniques, and/or compositions employed herein.

REFERENCES

Chen, W-J., Andres, D. A., Goldstein, J. L., Russell, D. W. and Brown, M. S. (1991) *Cell* 66, 327–384.

Finegold, A. A., Johnson, D. I., Farnsworth, C. C., Gelb, M. H., Judd, S. R., Glomset, J. A., and Tamanoi, F. (1991) *Proc. Natl. Acad. Sci. USA* 88, 4448–4452.

Finegold, A. A., Schafer, W. R., Rine, J., Whiteway, M and Tamanoi, F. (1990) *Sciences* 249, 165–169.

Goodman, L. E., Judd, S. R., Farnsworth, C. C., Powers, S., Gelb, M. H., Glomset, J. A., and Tamanoi, F. (1990) *Proc. Natl. Acad. Sci, USA* 87, 9665–9669.

Goodman, L. E., Perou, C. M., Fujiyama, A. and Tamanoi, F. (1988) *Yeast* 4, 271–281.

He, B., Chen, P., Chen, S. Y., Vancura, K. L., Michaelis, S. and Powers, S. (1991) *Proc. Natl. Acad. Sci USA* 88, 11373–11377.

Kohl, N. E., Diehl, R.e., Schaber, M. D., Rands, E., Soderman, D. D., He, B., Moores, S., pompllano, D. L., Ferro-Novick, S., Powers, S., Thomas, K. A., and Gibbs, J. B. (1991) *J. Biol. Chem.* 226, 18884–18888.

Magee, T. and Hanley, M. (1988) *Nature* (London) 335, 114–115.

Ochs, D. (1963) *Anal. Biochem.* 135, 470–474.

Reiss, Y., Goldstein, J. L. Seabra, M., Cassey, P. J. and Brown, M. S. (1990) *Cell* 62, 81–88.

Schaber, M. D., O'Hara, M. B., Garsky, V. M., Mosser, S. D., Bergstronm, Moores, S. L., Marshall, M. S. Friedman, P. A., Dixon, R. A. F. and Gibbs, J. B. (1990) *J. Biol. Chem.* 265, 14701–14704.

Schafer, W. R. Trueblood, C. E., Yang, C. C., Mayer, M. P., Rosenberg, S., Poulter, C. D. Kim, S. H., and Rine, J. (1990) *Science* 249, 1133–1139.

Seabra, M. C., Reiss, Y., Casey, P. J. Brown, M. S. and Goldstein, J. L. (1991) *Cell* 65, 429–434.

Seagel, I. H. (1976) *Biochemical Calculations*, 2nd Ed., John Wiley and Sons, N.Y.

Sherman, F., Fink, G. and Hicks, J. B. (1986) in *Methods in Yeast Genetics* pp. 163–167, Cold Spring Harbor Laboratory, New York.

Sherman F. et al. (1986) *Methods in Yeast Genetics*, Cold Spring Harbour Laboratory, N.Y.

Smith, P. K., Krohn, R. I. Hermanson, G. T., Mallis, A. K. Gartner, F. H., Provenzano, M. D. Fujimoto, E. K. Goeks, N. M., Olson, B. J., Klenk, D. C. (1985) *Anal. Biochem.* 150, Strathern, J. N. et al. (1981), *The Molecular Biology of the Yeast Saccharmyces*, Cold Spring Harbor Laboratory, N.Y.

Summers, M. D. and Smith, G. E. (1987) *Tex. Agric. Exp. Stn. Bull.* 1555.

Tamanoi, F. Hsueh, E. C., Goodman, L. E., Cobitz, A. R., Detrick, R. J., Brown, W. R. and Fujiyama, A. (1988) *J. Cell Biochem.* 36:261–273.

Toda, T., Uno, I. Ishikawa, T., Powers, S. Kataoka, T., Brosk, D., Cameron, S., Broach, J., Matsumoto, K. and Wigler, M. (1985) *Cell* 40, 27–36.

Yokoyama, K., Goodwin, G., Ghomashchi, F., Glomset, J. A., and Gelb,-M. H., (1991) *Proc. Natl. Acad. Sci, USA* 88, 5302–5306.

We claim:

1. A composition comprising isolated and purified yeast farnesyltransferase, wherein said farnesyltransferase has the following properties:

a) is a heterodimer having an estimated approximate molecular weight of 90 kDa comprising two subunits of 43 kDa and 34 kDa, respectively;

b) exhibits an optimum pH of approximately 7.8;

c) exhibits an optimum temperature of approximately 50°;

d) is inhibited by contact with a peptide containing a C-terminal CAAX wherein C designates cystsine, A designates an aliphatic amino acid and X designates any amino acid; and e) exhibits only two bands after SDS-PAGE that correspond to the two subunits of a.

2. The composition of claim 1, wherein the farnesyltransferase is further defined as having a specific activity of at least 230,000 in a farnesyltransferase assay.

3. The composition of claim 1, wherein the farnesyltransferase is further defined as showing a $K_m$ of 5.1 µM for the substrate GST-CIIS and $K_n$ of 39 µM for the substrate GST-CIIL.

4. The composition of claim 1 further comprising a buffer.

5. The composition of claim 4, wherein the buffer is tris-HCl at a pH of about 8.0.

* * * * *

UNITED STATES PATENT AND TRADEMARK OFFICE
CERTIFICATE OF CORRECTION

PATENT NO. : 5,578,477
DATED : November 26, 1996
INVENTOR(S) : Fuyuhiko Tamanoi

Page 1 of 2

It is certified that error appears in the above-indentified patent and that said Letters Patent is hereby corrected as shown below:

In the Title Page

In column 2, after line 1, insert:

--FOREIGN PATENT DOCUMENTS 0 456 474 A1   11/91   European Pat. Off.--

In column 2, after line 2, under "OTHER PUBLICATIONS" insert:

--   Finegold et al, Science, 249:165-169 (1990).
        Gomez et al., Biochemical Journal, 289:25-31 (1993).
        Zeeck et al., The Journal of Antibiotics, XL(11),
            1530-1540 (1987).
        Buzzetti et al., Pharmaceutica Acta Helvetiae,
            38:871-874 (1963).
        Van Der Pyl et al., The Journal of Antibiotics, 45
            (11):1802-1805 (1992).
        Chen et al., Cell, 66:327-334 (1991).
        Finegold et al., PNAS, 88:4448-4452 (1991).
        Goodman et al., PNAS, 87:9665-9669 (1990).
        Goodman et al., Yeast, 4:271-281 (1988).
        He et al., PNAS, 88:11373-11377 (1991).

UNITED STATES PATENT AND TRADEMARK OFFICE
CERTIFICATE OF CORRECTION

PATENT NO.    : 5,578,477
DATED         : November 26, 1996
INVENTOR(S)   : Fuyuhiko Tamanoi Page 2 of 2

It is certified that error appears in the above-indentified patent and that said Letters Patent is hereby corrected as shown below:

In the Title Page (cont'd)

```
     Kohl et al., The Journal of Biological Chemistry,
          266:18884-18888 (1991).
     Magee et al., Nature, 335:314-315 (1988).
     Reiss et al., Cell, 62:81-88 (1990).
     Schaber et al., The Journal of Biological Chemistry,
          265:14701-14704 (1990).
     Schafer et al., Science, 249:1133-1139 (1990).
     Seabra et al., Cell, 65:429-434 (1991).
     Tamanoi et al., Journal of Cellular Biochemistry,
          36:261-273 (1988).
     Yokoyama et al., PNAS, 88:5302-5306 (1991). --.
```

In the Claims

In claim 3, line 3, replace "$K_n$" with --$K_m$--.

Signed and Sealed this

Thirty-first Day of August, 1999

*Attest:*

Q. TODD DICKINSON

*Attesting Officer*          *Acting Commissioner of Patents and Trademarks*